United States Patent
Rathjen (10) Patent No.: US 7,434,933 B2
(45) Date of Patent: *Oct. 14, 2008

(54) DEVICE AND METHOD FOR DETERMINING GEOMETRIC MEASUREMENT VALUES OF AN EYE

(75) Inventor: Christian Rathjen, Bremen (DE)

(73) Assignee: Sis AG Surgical Instrument Systems (CH)

( * ) Notice: Subject to any disclaimer, the term of this patent is extended or adjusted under 35 U.S.C. 154(b) by 802 days.

This patent is subject to a terminal disclaimer.

(21) Appl. No.: 10/396,564

(22) Filed: Mar. 26, 2003

(65) Prior Publication Data

US 2003/0189689 A1 Oct. 9, 2003

(30) Foreign Application Priority Data

Apr. 5, 2002 (EP) .................................. 02405272

(51) Int. Cl.
*A61B 3/14* (2006.01)
*A61B 3/10* (2006.01)

(52) U.S. Cl. .................. 351/208; 351/206; 351/221; 351/246

(58) Field of Classification Search .................. 351/200, 351/205, 246

See application file for complete search history.

(56) References Cited

U.S. PATENT DOCUMENTS

| 4,761,071 | A | * | 8/1988 | Baron | 351/212 |
|---|---|---|---|---|---|
| 5,404,884 | A | * | 4/1995 | Lempert | 600/476 |
| 5,757,462 | A | * | 5/1998 | Nanjo | 351/206 |
| 5,867,250 | A | | 2/1999 | Baron | |
| 5,886,767 | A | | 3/1999 | Snook | |
| 6,190,317 | B1 | * | 2/2001 | Hayafuji | 600/405 |
| 6,234,631 | B1 | | 5/2001 | Sarver et al. | |
| 6,286,958 | B1 | * | 9/2001 | Koest et al. | 351/214 |
| 6,526,160 | B1 | * | 2/2003 | Ito | 382/117 |
| 7,264,355 | B2 | * | 9/2007 | Rathjen | 351/221 |
| 7,280,678 | B2 | * | 10/2007 | Haven et al. | 382/117 |
| 2002/0154269 | A1 | * | 10/2002 | Liu et al. | 351/206 |

FOREIGN PATENT DOCUMENTS

WO WO 01/62140 A1 8/2001

* cited by examiner

*Primary Examiner*—Jordan M Schwartz
(74) *Attorney, Agent, or Firm*—Ostrolenk, Faber, Gerb & Soffen, LLP (57) ABSTRACT

A device for determining geometric measurement values of an eye, in particular a human eye, comprises a light projector for projecting a beam of rays through a section of the eye and image capturing means for capturing two images of a partial region of the section illuminated by the light projector at two angles of observation from two different positions outside the beam of rays. The device comprises moreover image processing means for determining the cornea from the two images and for determining the corneal thickness from the two images. The device furthermore comprises processing means for calculating the thickness of the actual cornea of the eye directly from the corneal thickness determined from the first image and from the corneal thickness determined from the second image through formation of weighted mean values.

27 Claims, 2 Drawing Sheets

DEVICE AND METHOD FOR DETERMINING GEOMETRIC MEASUREMENT VALUES OF AN EYE

BACKGROUND OF THE INVENTION

1. Field of the Invention

The present invention relates to a device and a method for determining geometric measurement values of an eye. In particular, the invention relates to a device and a method for determining geometric measurement values of a human eye in which, by means of a light projector, a beam of rays is projected through a section of the eye, in which a first image of at least a partial region of the section illuminated by the light projector is registered, by means of image capturing means, at a first observation angle, from a first position outside the beam of rays, and in which a second image of the partial region is registered, by means of the image capturing means, at a second observation angle, from a second position outside the beam of rays.

2. Description of Related Art

Described in the printed patent specification U.S. Pat. No. 6,234,631 is a method for measuring the anterior and posterior corneal surfaces and the corneal thickness of the eye. In the method according to U.S. Pat. No. 6,234,631, a front-view camera is used to capture a front view, and, symmetrically thereto, a left and a right camera to capture two side views of the eye. The left and the right camera are each oriented at a 45-degree-angle to the optical axis of the front-view camera. In the method according to U.S. Pat. No. 6,234,631, a light pattern in the shape of a cross, similar to two simultaneously projected orthogonal slits, is projected onto the cornea, and the iris is illuminated with infrared light for contrasting the pupil. The horizontal portion of the light cross is captured with the front-view camera, and the vertical portion of the light cross is captured by each of the left and right cameras. At the same time an image of the pupil is captured by each of the three cameras. From the pupil images, the pupil contour is determined from the viewpoint of each of the three cameras. From the images of the light cross, and with assumption of an approximate corneal surface, a first approximate value is calculated for the corneal thickness on the basis of the ray trajectory light source . cornea . camera, by means of so-called ray tracing, according to U.S. Pat. No. 6,234,631. This first approximate value serves as an initial value for an iterative procedure in which, starting from the previously determined topography of the anterior corneal surface, the corneal thickness and the topography of the posterior corneal surface are determined. Determination of the topography of the anterior corneal surface takes place through iterative calculation from images of reflections of a placido disc on the cornea, which are taken by means of the three cameras. The corneal thickness and the topography of the posterior corneal surface are calculated, according to U.S. Pat. No. 6,234,631, iteratively on the basis of the ray trajectory pupil contour . cornea . camera (ray tracing), the views of each of the three cameras being taken into consideration.

Described in the published patent application WO 01/62140 is a system to measure the topography of both corneal surfaces and the corneal thickness. In the system according to WO 01/62140, a light beam, for example a laser beam, expanded in a fan shape by means of a cylindrical lens, is shone on the cornea. The system is designed such that the fan-shaped light beam can be rotated. The illuminated region in the area of intersection of the fan-shaped light beam and of the cornea is captured by two cameras, which are disposed at right angles to one another, so that their directions of observation include a 90 degree angle in the direction of view of the optical axis of the eye. The pictures taken by the cameras of the illuminated section are each undistorted only when the plane of the section lies perpendicular (seen in the direction of the optical axis of the eye) to the direction of observation of the respective camera. The other camera registers the section in this position from above, and thus can record neither the thickness nor the profile of the cornea. In the system according to WO 01/62140, a corrected, undistorted image is generated from the images of the two cameras, the undistorted image corresponding to that of a virtual rotating camera. The thickness of the cornea is then determined from the corrected image. Through rotation of the light source, the corneal topography can be put together from a multiplicity of corrected images.

For calculation of the corneal thickness by means of ray tracing, the surface inclination of the cornea must also be known, in addition to the refraction index of the cornea, the angle of illumination (directions of the projected light beams), and the observation angle (direction of the registered light beams). The refraction index can be assumed to be known, and both the illumination and the observation angles can be determined through calibration of the system according to WO 01/62140. For determination of the surface inclination, however, the system according to WO 01/62140 requires additional means if the influence of the surface inclination of the cornea is not supposed to falsify the result of the thickness calculation according to WO 01/62140.

SUMMARY OF THE INVENTION AND OBJECTS

It is an object of the present invention to propose a new device and a new method for determining geometric measurement values of an eye, the design and execution of which are simpler than the state of the art, and in particular do not require any additional, special means for determining the surface inclination of the cornea.

The device for determining geometric measurement values of an eye, in particular a human eye, comprises a light projector for projection of a beam of rays through a section of the eye, and image capturing means for capturing a first image of at least a partial region of the section, illuminated by the light projector, at a first observation angle, from a position outside the beam of rays, and for capturing a second image of the partial region at a second observation angle, from a second position outside the beam of rays.

The above-mentioned objects are achieved through the invention in particular in that this device comprises image processing means to identify eye structures from the first captured image, to identify eye structures from the second captured image, to measure a first distance between the eye structures identified from the first image and to measure a second distance between the eye structures identified from the second image, and in that this device comprises processing means to calculate at least one of the geometric measurement values directly from the measured first distance and the measured second distance.

With determination of the first and second distance from two images of the illuminated section, e.g. a so-called light section, from two independent positions with known observation angles, there result, with known refraction index, two equations with two unknowns which can be calculated from these equations, i.e. the surface inclination angle of the cornea and the distance between the actual structures in the eye corresponding to the imaged eye structures. The advantage of the device designed in this way to determine distances between eye structures and surface inclination angles of the cornea as geometric measurement values of an eye lies in particular in its simplicity. A further advantage of this device is that no estimates of, or assumptions about, the surface inclination angle of the cornea have to be made for determining distances between eye structures. Thus, for example, an opened corneal flap can be measured, i.e. a piece of cornea in any position. The device requires neither additional special means for determining the surface inclination of the cornea nor numerous cameras, nor special additional infrared light sources, and it also does not need numerous iteration steps, taking up both time as well as calculating capacity and memory space. Since the eye structures are captured from two angles of observation, determination of geometric measurement values can also take place, exceptionally, even when one of the two images has shadows.

In a preferred embodiment variant, the processing means of the device are designed to determine, from the measured first distance and the measured second distance, the distance between the actual eye structures, i.e. between the structures in the eye corresponding to the eye structures identified from the first and the second image, preferably through formation of weighted mean values from the measured first distance and the measured second distance.

Preferably, the image processing means are designed to identify the cornea from the first captured image, to identify the cornea from the second captured image, to take a first distance measurement of the cornea identified from the first image and to take a second distance measurement of the cornea identified from the second image, and the processing means are designed to calculate the thickness of the actual cornea from the first distance measurement taken and the second distance measurement taken. The above-mentioned advantages can thus be achieved with such a device for measurement of the corneal thickness.

In a preferred embodiment variant, the processing means are designed additionally, or alternatively, to calculate an angle of inclination between the beam of rays and the normal to the surface, turned toward the light projector, of the actual cornea from the measured first distance and the measured second distance. The device can thus be used not only to measure distances between eye structures, in particular to measure the corneal thickness, but also to measure the surface inclination of the cornea.

Preferably, the first position and the second position of the image capturing means lie on different sides of a plane in which the beam of rays is situated, and the first and the second angles of observation are of equal size. The advantage of selecting the two angles of observation so as to be of equal size is that a precise determination of the surface inclination of the cornea is not necessary since small deviations from an assumed or estimated surface inclination do not have an effect upon the mean value calculated from the measured first distance and the measured second distance when the device is applied such that the beam of rays goes approximately through a meridional section of the cornea. In the formation of mean values, the differences in the measurement of the first distance between the eye structures from the first image and of the second distance between the eye structures from the second image namely cancel each other out. That means that the deviations in the distances measured from two different perspectives cancel each other out. If therefore the device is used in such a way that the beam of rays is projected substantially perpendicular to the (corneal) surface, turned toward the light projector, of the eye, slight angular misalignments of the beam of rays with respect to the normal to the surface, turned toward the light projector, of the cornea do not have an effect upon the determination of the corneal thickness. Even when the device is applied such that the beam of rays is projected substantially perpendicular through the vertex of the cornea (i.e. through the optical axis of the eye), slight angular misalignments (i.e. inclination away from the normal) and eccentricities (i.e. shifting from the vertex) of the beam of rays do not have an effect upon the determination of the corneal thickness. The same applies to small deviations of the first observation angle to the second observation angle. Angular misalignments of the light projector also have a less crucial effect upon the measurement. Thus the advantage of equal observation angles is that small inaccuracies in the application, the adjustment and/or the calibration of the device do not result in any large deviations in the measuring results. If the device is applied in meridional sections, for example, then a calibration in meridional section suffices in order to be able to measure precisely even with slight eccentricities and angular misalignments. The device thus makes possible a simpler application and design while maintaining the precision of the measuring results.

In an embodiment variant, the processing means are designed to calculate an angular misalignment factor from the measured first distance and the measured second distance, which angular misalignment factor indicates the magnitude of the angular misalignment of the beam of rays with respect to the normal to the surface, turned toward the light projector, of the actual cornea and the magnitude of the difference of the first observation angle from the second observation angle. Such an angular misalignment factor gives a gage for the quality of the application and the precision of the measurement. The angular misalignment factor can be shown to the user of the device so that a correction of the application or of the calibration of the device can be carried out. The processing means can also be designed such that they determine, in dependence upon the determined angular misalignment factor, weighting factors for the formation of mean values, so that the determination of the measurement values is automatically adjusted to the magnitude of the angular misalignment of the beam of rays, to the magnitude of the difference of the first observation angle from the second observation angle and/or to the surface inclination of the cornea.

In a preferred embodiment variant, the imaging means comprise an image converter, e.g. a CCD chip (Changed Coupled Device) of a camera, and the imaging means comprise optical elements for light ray redirection, first of the optical elements being disposed at the first position in such a way that light rays for generation of the first image are redirected to the image converter and second of the optical elements being disposed at the second position in such a way that light rays for generation of the second image are redirected to the image converter. The advantage of optical means for light ray redirection disposed in this way is that the first and the second image, i.e. the capturing of two perspectives of the light section, can be captured with a single common camera at the same time. A costly second camera and image capturing hardware can thereby be eliminated, synchronization of a plurality of image converters is unnecessary, and there results an especially compact device.

Preferably the light projector is designed such that it projects the beam of rays in the form of a plane of light. The plane of light, for example in the form of a projected light slit, is especially well suited to the generation of an illuminated light section in the eye, which can be captured as an image from two different positions such that respective eye structures can be easily associated to one another in the two images.

The image capturing means are preferably disposed in Scheimpflug configuration with respect to the beam of rays. The Scheimpflug configuration of the image capturing means has the advantage that the imaging is sharp over a large area along the beam of rays.

In an embodiment variant, the device comprises a rotation driver for rotating the image capturing means and the light projector about an axis running through the beam of rays. Through the rotation of the image capturing means and of the light projector preferably about the optical axis of the eye, geometric measurement values of the whole eye can be determined, in particular the corneal thickness. The high degree of symmetry and the measuring conditions remaining the same during the rotation about the optical axis of the eye have a positive effect upon the measurement precision.

BRIEF DESCRIPTION OF THE DRAWINGS

An embodiment of the present invention will be described in the following with reference to an example. The example of the embodiment is illustrated by the following attached figures.

DETAILED DESCRIPTION OF THE PREFERRED EMBODIMENTS

In the following description, it is to be kept in mind that, in referring to FIGS. 1 to 3, considerations relating to these figures are made in an exemplary way for the drawing plane, but considerations for planes parallel to the drawing plane are also valid, however. The term perpendicular relates to the drawing plane. In the case of light beams which do not lie in the plane of a meridian of the cornea, there is an additional beam component which stands out from the drawing plane. The functional interrelations of image creation hereby change depending upon the optical construction. Since this has no consequences for the above-mentioned advantages of the method, it will not be gone into any further separately.

Figure 1:
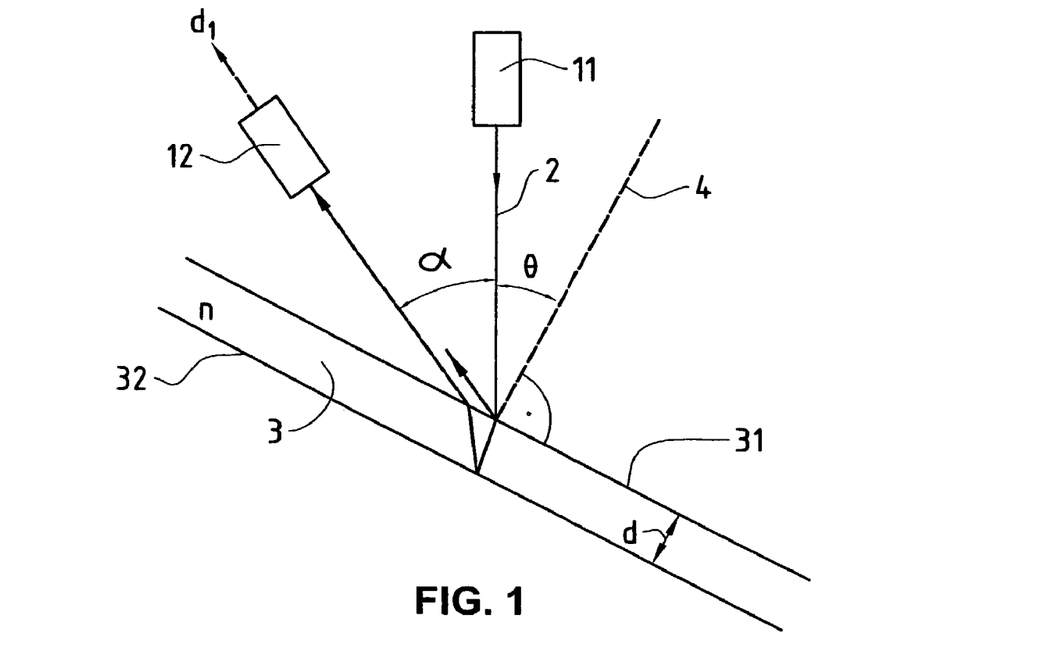
FIG. 1 shows in a schematic view the ray trajectory of a beam of rays projected by the light projector through the cornea of an eye and captured by image capturing means.

In FIG. 1, the reference numeral 3 relates to a simplified schematic illustration of an optically diffusive body, in particular a cornea, with the refraction index n and the thickness d. In FIG. 1 a light projector 11 projects a beam of rays 2 through the cornea 3. Corresponding to the structure of the beam of rays 2, a section of the cornea 3 is illuminated. It is to be mentioned here that the beam of rays 2 in practice has a spatial structure which is not represented in the schematic illustration of FIG. 1. Designated by the reference numeral 4 is a normal to the surface 31 of the cornea 3. The angle of incidence $\ominus$ indicates the angle between the beam of rays 2 and the surface normal 4. The reference numeral 12 designates an image capturing device with processing means, which captures the section illuminated in the cornea 3 at an observation angle α. According to the known law of refraction (Snell's Law), the lengths of path of the light rays covered in a transparent body, here the cornea 3, depend upon the refraction index of the transparent body and of the surrounding medium as well as upon the angle of incidence and the angle of reflection of the light rays. If, from the image of the section of the cornea 3 illuminated by the light projector 11, captured by the image capturing device 12, the distance $d_1$ is determined between the imaged anterior corneal surface 31 and the imaged posterior corneal surface 32, the thickness d of the actual cornea 3 can thus be calculated according to analytically or experimentally obtained equations (i) as a function of this determined distance $d_1$, of the angle of incidence $\ominus$, of the observation angle α and of the refraction index n (the influence of the thickness of the beam of rays was not cited here; the equation can also exist in implied form):

$$d = f(d_1, \ominus, \alpha, n) \quad (i)$$

Figure 2:
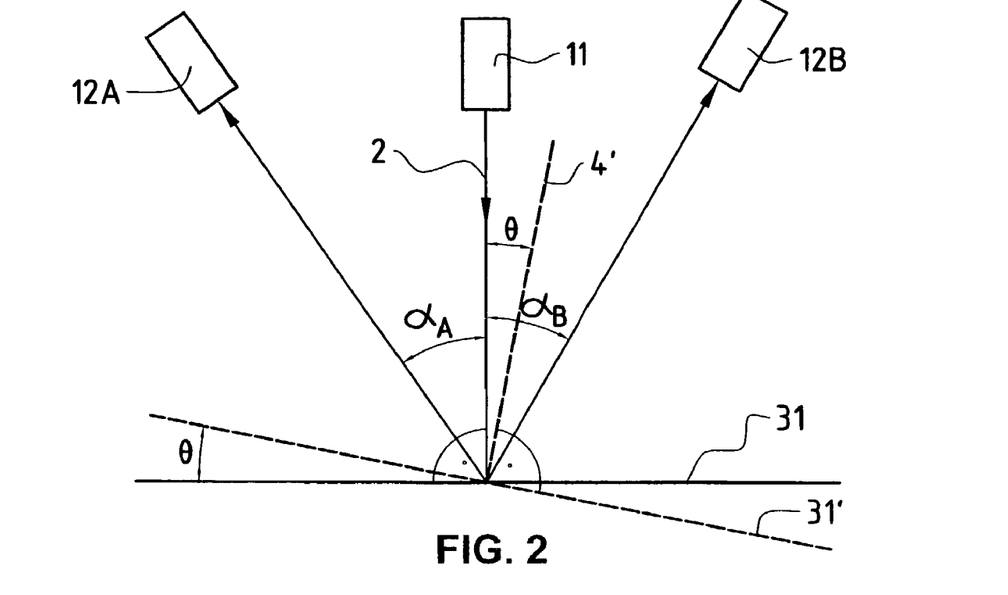
FIG. 2 shows in a schematic view a device configuration comprising a light projector for projection of a beam of rays and comprising two image capturing devices for capturing the section of the cornea illuminated by the light projector from two positions of observation.

In contrast to the device configuration shown in FIG. 1, the device configuration shown in FIG. 2 comprises two image capturing devices 12A and 12B, for instance CCD cameras (Charged Coupled Device) or CMOS cameras (Complementary Metal-Oxide-Silicon). Captured and imaged by the image capturing device 12A is the section of the cornea illuminated by the light projector 11 at the observation angle $\alpha_A$. Captured and imaged by the image capturing device 12B is the section of the cornea illuminated by the light projector 11 at the observation angle $\alpha_B$. The light projector 11 projects the beam of rays 2 preferably in the form of a plane of light, in particular as a projected light slit, so that a light section results as the illuminated section. The beam of rays 2 can also have a ray-shaped structure. The light projector 11 comprises, for example, a slit lamp or a laser, whose light is shaped into a fan by means of beam conversion optics. The angles of observation $\alpha_A$ and $\alpha_B$ can be different and can also be situated on the same side of the beam of rays. The two image capturing devices 12A and 12B are preferably positioned in a common plane perpendicular to the light plane, however. As is shown schematically in FIG. 2, the beam of rays 2 of the light projector 11 is projected through the cornea perpendicular (based on the drawing plane) to the corneal surface 31. If the corneal surface 31' has an inclination, shown by the broken line, with the surface inclination angle $\ominus$, however, then the beam of rays 2, is tilted from the surface normal 4' to the inclined corneal surface 31' by the corresponding angle of incidence $\ominus$.

From the two images of the illuminated section of the cornea from two different positions, the distance $d_A$ between the anterior and posterior corneal surface can be determined from the image of the image capturing device 12A, and the distance $d_B$ between the anterior and posterior corneal surface can be determined from the image of the image capturing device 12B. Since the observation angles $\alpha_A$ and $\alpha_B$ are known from the geometry of the device configuration and since the refraction index n is likewise known, two equations (i) result with two unknowns for calculation of the thickness d of the actual cornea and of the angle of incidence $\ominus$, which corresponds to the surface inclination angle $\ominus$ of the cornea.

Preferably the two image capturing devices 12A and 12B are arranged such that the observation angles $\alpha_A$ and $\alpha_B$ have the same value and the projection is substantially perpendicular to the corneal surface 31. The configuration with equal observation angles $\alpha_A$ and $\alpha_B$ makes possible a precise determination of the thickness d of the cornea 3, without having to determine precisely the surface inclination angle $\ominus$ or respectively the incidence angle ⊖. If a Taylor series is set up for the measured distances $d_A$ and $d_B$ according to the equations ($ii_A$, $ii_B$):

$$d_A = d_{A(\theta=0)} + \frac{\partial d_A}{\partial \theta} d\theta + \frac{1}{2} \frac{\partial^2 d_A}{\partial \theta^2} d\theta^2 + \ldots \quad (ii_A)$$

$$d_B = d_{B(\theta=0)} + \frac{\partial d_B}{\partial \theta} d\theta + \frac{1}{2} \frac{\partial^2 d_B}{\partial \theta^2} d\theta^2 - \ldots \quad (ii_B)$$

it is permissible to terminate the series after the second term, for small deviations in surface inclination angle ⊖ or respectively incidence angle ⊖. In calculating the arithmetic mean from the accordingly reduced Taylor series for the measured distance $d_A$ and for the measured distance $d_B$, a deviation d⊖ does not have an effect since such a deviation is registered from the different positions of the two image capturing devices 12A and 12B in each case as an angle with differing sign, and deviations thus cancel each other out. If, for example, in the case of a planned perpendicular projection of the beam of rays 2 through the vertex S of the cornea (see FIG. 3), a lateral shifting occurs with respect to the vertex S (i.e. an eccentricity) by one millimeter in the actual application, the measurement deviations at the shifted point of measurement caused by the corresponding surface inclination angle ⊖ are reduced by at least a factor of ten compared with a measurement from just one position with just one image capturing device 12. Thus for an observation angle of 45° the measurement deviations in the case of eccentricity of up to one millimeter (or respectively in the case of corresponding angular misalignments) are clearly kept under five micrometers.

Figure 3:
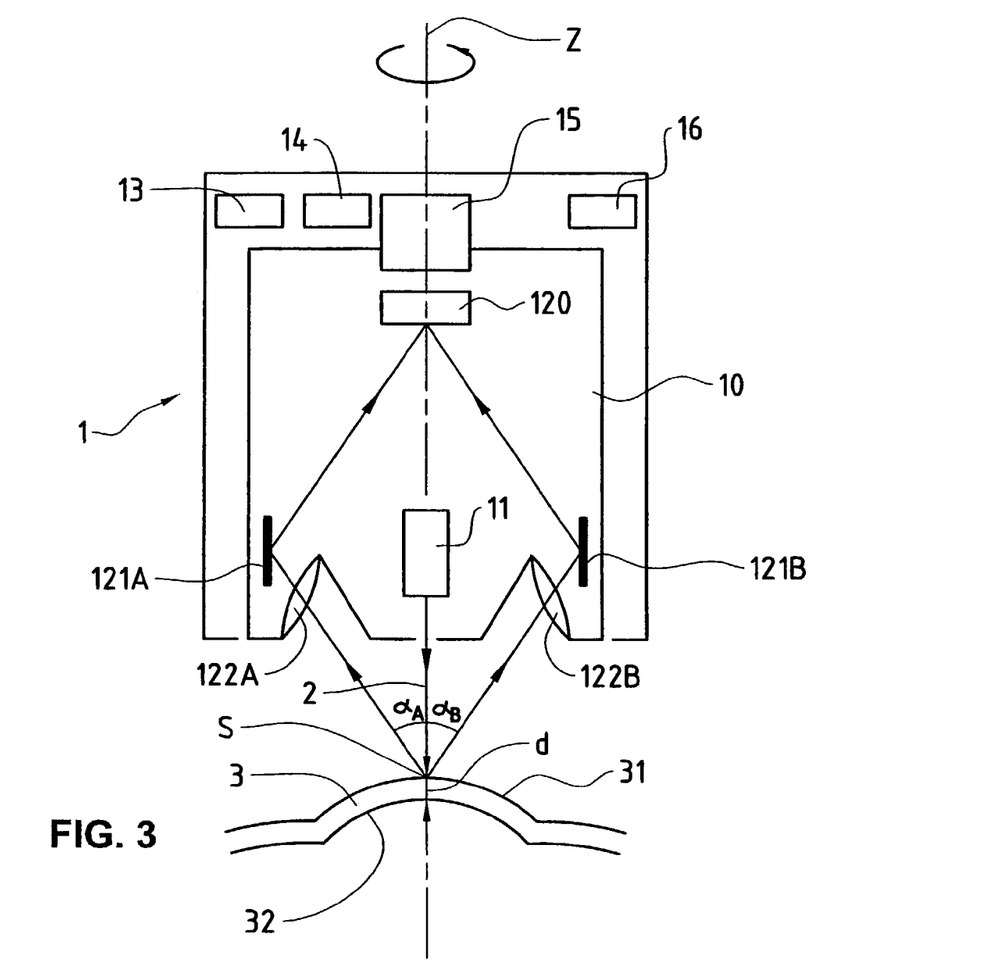
FIG. 3 shows in a schematic view a device for determining geometric measurement values of an eye, which projects a beam of rays through the cornea and which captures the section of the cornea illuminated by the beam of rays from two positions of observation.

In FIG. 3, the reference numeral 1 designates a preferred embodiment of the device for determining geometric measurement values of an eye. The elements in FIG. 3 having the same reference numerals as in FIG. 2 correspond to those of the device configuration of FIG. 2. In FIG. 3, the device 1 is applied such that the beam of rays 2 is projected by the light projector 11 substantially perpendicular to the anterior corneal surface 31 through the vertex S of the cornea 3. As in the device configuration according to FIG. 2, the section of the cornea 3 illuminated by the beam of rays 2 is registered and imaged by the device 1 from two different positions. However, the image capturing means of device 1 differ from those in the device configuration of FIG. 2 in that they comprise just one (single) joint image converter 120. The image capturing means of device 1 comprise moreover ray-imaging optical elements 122A and 122B, for example objectives or lenses, and ray-redirecting optical elements 121A and 121B, for example mirrors. As shown schematically in FIG. 3, a ray-imaging element 122A or respectively 122B and a ray-redirecting element 121A, or respectively 121B, are each disposed in pairs in such a way that light rays of the illuminated section of the cornea 3 are imaged, with an observation angle $\alpha_A$, or respectively $\alpha_B$, through the ray-imaging elements 122A, or respectively 122B, in the direction of the ray-redirecting elements 121A, or respectively 121B, and that these light rays are redirected to the joint image converter 120 by the ray-redirecting elements 121A, or respectively 121B. The observation angles $\alpha_A$ and $\alpha_B$ preferably have the same value. As shown schematically in FIG. 3, the ray-imaging elements 122A and 122B and the ray-redirecting elements 121A and 121B are preferably symmetrically disposed (to the optical axis Z of the eye) in a plane perpendicular to the plane of light. The image converter 120, for instance a CCD chip, is preferably disposed in a Scheimpflug configuration with respect to the beam of rays 2. One skilled in the art will understand that the arrangement of the optical elements shown in FIG. 3 is only one of many possible configurations for generating on a joint image converter 120 two images of at least a partial region of the section of the cornea 3 illuminated by the light projector 11 at two observation angles $\alpha_A$ and $\alpha_B$. It would also be possible, for example, to dispose mirrors in front of the lenses, to use further mirrors and lenses, to use mirror optics and/or to dispose the optical elements asymmetrically as well as make use of anamorphic images.

Figure 4:
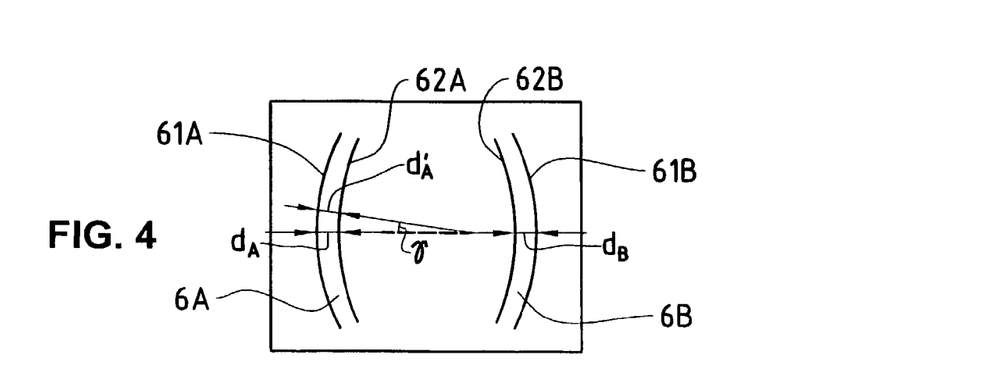
FIG. 4 shows a multiple image with a first and a second image of the illuminated section of the cornea of an eye.

In the joint image converter 120, a multiple image is generated with a first image 6A, taken at an observation angle $\alpha_A$, of the illuminated section of the cornea 3 and a second image 6B, taken at the observation angle $\alpha_B$, of the illuminated section of the cornea 3, as is shown schematically in FIG. 4 for a light section. Indicated by $d_A$ in FIG. 4 is that the thickness of the cornea can appear to taper toward the edge owing to the laws of image generation. This seeming change in the thickness can be taken into account in calculation of the actual thickness of the cornea 3 in that, for example, the angle γ is determined to the plane of symmetry of the light section. A correction function depending upon the angle γ can then correct the determined thickness value. In a simple way a calibration which, taken strictly, is only valid for the vertex S, can thereby be extended also to the lateral regions of the cornea. It is to be noted that with a differently selected working spacing the illuminated sections in the multiple image could also be superimposed (as indicated for the vertex S in FIG. 3). If the partial images cannot be separated via image processing methods, then, alternatively, an image separation be achieved optically, via filters (color filters with simultaneous use of a color camera) or shutters.

The device 1 comprises image processing means 13 with programmed software modules which control a processor of the device 1 in such a way that it executes the image processing functions described in the following. The image processing means 13 identify in each case from the captured first image 6A and the captured second image 6B defined eye structures such as the cornea, determined through the image of the anterior corneal surface 61A, or respectively 61B, and the image of the posterior corneal surface 62A, or respectively 62B, or the contours of the iris and the pupil (not shown), or other features such as the anterior chamber depth or the anterior chamber angle (not shown). Subsequently the image processing means 13 define distances between the identified imaged eye structures, such as the corneal thickness, i.e. the distance $d_A$ between the image of the anterior corneal surface 61A and the image of the posterior corneal surface 62A, or respectively the distance dB between the image of the anterior corneal surface 61B and the image of the posterior corneal surface 62B. FIG. 4 shows a preferred embodiment in which the distances are determined directly in the image of the cornea.

The device 1 comprises processing means 14 with programmed software modules, which control a processor of the device 1 in such a way that it executes the functions described in the following. From the distances determined by the image processing means 13, the processing means 14 calculate geometric measurement values of the eye, such as distances between the actual structures of the eye, in particular the corneal thickness d, or the surface inclination angle ⊖ of the cornea 3. In particular the processing means 14 calculate the corneal thickness d from the distance $d_A$ and the distance $d_B$ through formation of weighted mean values. The weighting factors for the formation of mean values result from the equation (i) with known refraction index n and with known observation angles. For example, with $\alpha_A=\alpha_B=\alpha$, and ⊖=0, for the case of parallel perspective, as a first approximation, the weighting factor c results from the equation (iii):

$$c = \frac{\sqrt{n^2 - \sin(\alpha)^2}}{\cos(\alpha)\sin(\alpha)} \quad \text{(iii)}$$

Based on the symmetry of the configuration, the weighting factors for $d_A$ und $d_B$ in this case are of equal size, and the corneal thickness d then results through weighted mean value formation according to the equation (iv):

$$d = c\frac{(d_B + d_A)}{2} \quad \text{(iv)}$$

The processing means 14, however, can also be designed such that they calculate from the distance $d_A$ and the distance $d_B$ the surface inclination angle ⊖ of the cornea 3, which, as already mentioned, corresponds to the incidence angle ⊖ between the beam of rays 2 and a normal 4 to the anterior corneal surface 31. In the above example, with known refraction index n and with known observation angles $\alpha_A = \alpha_B = \alpha$, for parallel perspective, the surface inclination angle ⊖ results from the equation (v):

$$\theta = \frac{\sin(\alpha)n}{\sqrt{n^2 - \sin(\alpha)^2}} \frac{(d_B - d_A)}{(d_B + d_A)} \quad \text{(v)}$$

The processing means 14 also calculate from the distance $d_A$ and the distance $d_b$ an angular misalignment factor k according to the equation (vi), which factor indicates the magnitude of the misalignment of the beam of rays 2 with respect to the normal 4 to the anterior corneal surface 31 (or respectively the magnitude of the eccentricity) and/or the magnitude of the difference of the observation angle $\alpha_A$ from the observation angle $\alpha_B$.

$$k = \frac{d_B - d_A}{d_B + d_A} \quad \text{(vi)}$$

As long as the angular misalignment factor k lies within a defined tolerance range, the processing means 14 use the weighted mean value formation for calculation of the corneal thickness d without adjusting the weighting factors to the misalignment.

In an embodiment variant, the weighting factors can be adjusted as a function of the angular misalignment factor.

In an embodiment variant, the processing means 14 show the angular misalignment factor k on the display 16 as an aid in application for the user of the device 1.

In calculating the corneal thickness d, the angular misalignment factor k can also be used by the processing means 14 as the basis for deciding with respect to the automatic switching over from a first calculating mode with weighted mean value formation to a second calculating mode, in which, in addition to the corneal thickness d, also the incidence angle ⊖ or respectively the surface inclination angle ⊖ of the cornea is assumed unknown, and two equations (i) are solved for the two image capturing devices 12A and 12B, or respectively for the corresponding image capturing means 120, 121A, 121B, 122A, 122B.

The processing means 14 can calculate the thickness of the cornea 3 and the surface inclination angle ⊖ for all points of the anterior corneal surface 31, which lie in the captured partial region of the illuminated section of the cornea 3.

In the device 1, the image converter 120, the ray-imaging elements 122A and 122B, the ray-redirecting elements 121A and 121B as well as the light projector 11 are accommodated in a rotatable carrier device 10 which is rotated about the optical axis Z of the eye by a rotation driver 15, for example an electromotor. Through the rotation of the light projector 11 and the image capturing means 120, 121A, 121B, 122A and 122B about the optical axis Z, the entire cornea 3 is measured. In this configuration, owing to the high symmetry, the slightest the lowest measurement uncertainty can be achieved.

The image processing means 13 and the processing means 14 comprise programmed software modules, which are executed on a joint processor or on a plurality of processors. For the purposes of the present text, the distinction between image processing means 13 and processing means 14 is of a purely conceptual nature, i.e. functions assigned to the image processing means 13 could also be assigned to the processing means 14 and vice-versa (such as e.g. the determination of distances). One skilled in the art will understand that the functions of the software modules of the image processing means 13 and of the processing means 14 can also be executed through hardware.

It should be mentioned here that the device 1 is preferably designed as a compact measuring probe, whereby the modules of the processing means 14 responsible for the calculation of the corneal thickness d, covering the entire surface, and of the surface inclination angle ⊖ can be implemented in an external processing unit, for instance in a personal computer, the data exchange with the device 1 taking place via a communication connection with or without contacts. Calculated values for the corneal thickness d and for the surface inclination angle ⊖ can be indicated on the display 16 or on a display of the external processing unit.

It is to be stated here furthermore that the device 1 can be extended to projection of a plurality of beams of rays. Moreover the images could be captured from more than two observation angles, but this only makes sense when additional parameters, such as, for example, the width of the beam of rays, are supposed to be registered (three equations with three unknowns). For better understanding it should also be said that the observation angle α ($\alpha_A$, $\alpha_B$) used in the description represents an observation beam. If central-perspectival images are used, a thus varies.

Finally, it is to be said that the statements made above about determination of the corneal thickness can also be applied to the determination of other distances.

LIST OF REFERENCE NUMERALS 1 device for determining geometric measurement values of an eye
2 beam of rays
3 cornea
4 normal
6A first image
6B second image
10 rotatable carrier device
11 light projector
12 image capturing device with processing means
12A, 12B image capturing device 13 image processing means
14 processing means
15 rotation driver
16 display
31, 31' anterior corneal surface
32 posterior corneal surface
61A, 61B image of the anterior corneal surface
62A, 62B image of the posterior corneal surface
120 image converter
121A, 121B ray-redirecting optical elements (mirrors)
122A, 122B ray-imaging optical elements (lenses)
$\alpha, \alpha_A, \alpha_B$ observation angle
d thickness (distance)
$d_A$ first distance
$d_A$ second distance
$d_1$ distance
n refraction index
$\ominus$ incidence angle (corresponding to surface inclination angle)
S vertex of the cornea
Z optical axis of an eye

The invention claimed is:

1. A device for determining geometric measurement values of an eye, comprising:
    a light projector for projection of a beam of rays through a section of the eye,
    imaging means for capturing at the same time a first cross-sectional image of at least a partial region of the section illuminated by the light projector, at a first observation angle, from a first position outside the beam of rays, and for capturing a second cross-sectional image of the partial region at a second observation angle, from a second position outside the beam of rays,
    image processing means configured to identify eye structures from the first cross-sectional image comprising at least a partial region of a cross-section of the eye illuminated by the light projector and captured at the first observation angle, to identify eye structures from the second cross-sectional image comprising at least a partial region of a cross-section of the eye illuminated by the light projector and captured at the second observation angle, to measure a first distance between the eye structures identified from the first cross-sectional image and to measure a second distance between the eye structures identified from the second cross-sectional image, and
    processing means to calculate at least one of said geometric measurement values from the first distance, measured in the first cross-sectional image, and the second distance, measured in the second cross-sectional image.

2. The device according to claim 1, wherein the processing means are configured to calculate a third distance between actual eye structures from the first distance and the second distance.

3. The device according to claim 2, wherein the processing means are configured to calculate from the first distance and the second distance the third distance between the actual eye structures through formation of weighted mean values.

4. The device according to claim 1, wherein the image processing means are configured to identify a cornea from the first cross-sectional image, to identify the cornea from a second cross-sectional image, to take a first distance measurement of the cornea identified from the first cross-sectional image and to take a second distance measurement of the cornea identified from the second cross-sectional image, and
    wherein the processing means are configured to calculate a thickness of an actual cornea from the first distance measurement of the cornea and the second distance measurement of the cornea.

5. The device according to claim 1, wherein the image processing means are configured to identify a cornea from the first cross-sectional image, to identify the cornea from the second cross-sectional image, to take a first distance measurement of the cornea identified from the first cross-sectional image and to take a second distance measurement of the cornea identified from the second cross-sectional image, and
    wherein the processing means are configured to calculate from the first distance measurement of the cornea and the second distance measurement of the cornea an angle of inclination between the beam of rays and a normal to the surface, turned toward the light projector, of an actual cornea.

6. The device according to claim 1, wherein the first position and the second position lie on different sides of a plane in which the beam of rays is situated, and
    wherein the first and the second observation angles are equal in size.

7. The device according to claim 1, wherein the image processing means are configured to identify a cornea from the first cross-sectional image, to identify the cornea from the second cross-sectional image, to take a first distance measurement of the cornea identified from the first cross-sectional image and to take a second distance measurement of the cornea identified from the second cross-sectional image, and
    wherein the processing means are configured to calculate an angular misalignment factor from the first distance measurement of the cornea and from the second distance measurement of the cornea, which angular misalignment factor indicates the magnitude of the angular misalignment of the beam of rays with respect to the normal to the surface, turned toward the light projector, of an actual cornea and the magnitude of the difference of the first observation angle from the second observation angle.

8. The device according to claim 1, wherein the image processing means are configured to identify a cornea from the first cross-sectional image, to identify the cornea from the second cross-sectional image, to take a first distance measurement of the cornea identified from the first cross-sectional image and to take a second distance measurement of the cornea identified from the second cross-sectional image, wherein the processing means are designed to calculate a thickness of an actual cornea from the first distance measurement of the cornea and the second distance measurement of the cornea through formation of weighted mean values,
    wherein the processing means are configured to calculate an angular misalignment factor from the first distance measurement of the cornea and the second distance measurement of the cornea, which angular misalignment factor indicates the magnitude of the angular misalignment of the beam of rays with respect to the normal to the surface, turned toward the light projector, of the actual cornea and the magnitude of the difference of the first observation angle from the second observation angle, and
    wherein the processing means are configured to determine weighting factors for the formation of mean values depending upon the determined angular misalignment factor.

9. The device according to claim 1, wherein the imaging means comprise an image converter and the imaging means comprise optical elements for light ray redirection, first of said optical elements being disposed at the first position in such a way that light rays for generation of the first image are redirected to the image converter and second of said optical elements being disposed at the second position in such a way that light rays for generation of the second image are redirected to the image converter.

10. The device according to claim 1, wherein the light projector is designed such that it projects the beam of rays in the form of a plane of light.

11. The device according to claim 1, wherein the imaging means are disposed in a Scheimpflug configuration with respect to the beam of rays.

12. The device according to claim 1, further comprising a rotation driver for rotation of the light projector and the imaging means about an axis running through the beam of rays.

13. A method for determining geometrical measurement values of an eye, the method comprising:
    projecting a beam of rays through a section of the eye by means of a light projector,
    capturing at the same time a first cross-sectional image of at least a partial region of the section illuminated by the light projector at a first observation angle, from a first position outside the beam of rays, and a second cross-sectional image of the partial region at a second observation angle from a second position outside the beam of rays,
    identifying eye structures from the first ,cross-sectional image comprising at least a partial region of a cross-section of the eye illuminated by the light projector and captured at the first observation angle,
    identifying eye structures from the second cross-sectional image comprising at least a partial region of a cross-section of the eye illuminated by the light projector and captured at the second observation angle,
    measuring a first distance between the eye structures identified from the first cross-sectional image,
    measuring a second distance between the eye structures identified from the second cross-sectional image,
    calculating from the first distance, measured in the first cross-sectional image, and the second distance, measured in the second cross-sectional image, at least one of the geometric measurement values, and
    displaying the at least one of the geometric measurement values.

14. The method according to claim 13, wherein a third distance between actual eye structures is calculated from the first distance and the second distance.

15. The method according to claim 14, wherein the third distance between the actual eye structures is calculated from the first distance and the second distance through formation of weighted mean values.

16. The method according to claim 13, wherein a cornea is identified from the first cross-sectional image, the cornea is identified from the second cross-sectional image, a first distance measurement is taken of the cornea identified from the first cross-sectional image, a second distance measurement is taken of the cornea identified from the second cross-sectional image, and a thickness of an actual cornea is calculated from the first distance measurement of the cornea and from the second distance measurement of the cornea.

17. The method according to claim 13, wherein a cornea is identified from the first cross-sectional image, the cornea is identified from the second cross-sectional image, a first distance measurement is taken of the cornea identified from the first cross-sectional image, a second distance measurement is taken of the cornea identified from the second cross-sectional image, and an angle of inclination between the beam of rays and a normal to the surface, turned toward the light projector, of an actual cornea is calculated from the first distance measurement of the cornea and the second distance measurement of the cornea.

18. The method according to claim 13, wherein the first position and the second position are selected on different sides of a plane in which the beam of rays is situated, and the first and the second observation angles are selected as equal in size.

19. The method according to claim 13, wherein the beam of rays is projected substantially perpendicular to the eye surface turned toward the light projector.

20. The method according to claim 13, wherein a cornea is identified from the first cross-sectional image, the cornea is identified from the second cross-sectional image, a first distance measurement is taken of the cornea identified from the first cross-sectional image, a second distance measurement is taken of the cornea identified from the second cross-sectional image, and an angular misalignment factor is calculated from the first distance measurement taken of the cornea and from the second distance measurement taken of the cornea, which angular misalignment factor indicates the magnitude of the angular misalignment of the beam of rays with respect to the normal to the surface, turned toward the light projector, of an actual cornea and the magnitude of the difference of the first observation angle from the second observation angle.

21. The method according to claim 13, wherein a cornea is identified from the first cross-sectional image, the cornea is identified from the second cross-sectional image, a first distance measurement is taken of the cornea identified from the first cross-sectional image, a second distance measurement is taken of the cornea identified from the second cross-sectional image, and a thickness of an actual cornea is calculated from the first distance measurement taken of the cornea and the second distance measurement taken of the cornea through formation of weighted mean values, an angular misalignment factor is calculated from the first distance measurement taken of the cornea and from the second distance measurement taken of the cornea, which angular misalignment factor indicates the magnitude of the angular misalignment of the beam of rays with respect to the normal to the surface, turned toward the light projector, of the actual cornea and the magnitude of the difference of the first observation angle from the second observation angle, and weighting factors for the formation of mean values are determined depending upon the determined angular misalignment factor.

22. The method according to claim 13, wherein first optical elements are disposed at the first position in such a way that they redirect light rays to an image converter to capture the first cross-sectional image, and second optical elements are disposed at the second position in such a way that they redirect light rays to the image converter to capture the second cross-sectional image.

23. The method according to claim 13, wherein the beam of rays is projected by the light projector in the form of a plane of light.

24. The method according to claim 13, wherein the images are captured by means of image capturing means in Scheimpflug configuration with respect to the beam of rays.

25. The method according to claim 13, wherein an image capturing means, for capturing the images, and the light projector are rotated about an axis running through the beam of rays.

26. The device of claim 1, wherein the image processing means are configured to identify as eye structures at least one of cornea, anterior corneal surface, posterior corneal surface, contours of an iris, contours of a pupil and anterior chamber of the eye.

27. The method of claim 13, wherein identifying eye structures include identifying as eye structures at least one of cornea, anterior corneal surface, posterior corneal surface, contours of an iris, contours of a pupil and anterior chamber of the eye.

* * * * *